United States Patent [19]
Deghenghi

[11] Patent Number: 6,025,471
[45] Date of Patent: Feb. 15, 2000

[54] DIAZASPIRO, AZEPINO AND AZABICYCLO THERAPEUTIC PEPTIDES

[76] Inventor: Romano Deghenghi, Chesaux-Dessus, St. Cergue, Switzerland, 1264

[21] Appl. No.: 09/089,954

[22] Filed: Jun. 3, 1998

[51] Int. Cl.$^7$ .................................................. C07K 7/00
[52] U.S. Cl. ........................... 530/330; 530/329; 514/17; 540/484
[58] Field of Search .................. 514/18, 19, 17; 530/330, 331, 329; 540/484

[56] References Cited

FOREIGN PATENT DOCUMENTS

| WO 96/15148 | 5/1996 | WIPO . |
| WO 97/01957 | 1/1997 | WIPO . |
| WO 98/22124 | 5/1998 | WIPO . |

OTHER PUBLICATIONS

C. Bowers, "Xenobiotic Growth Hormone Secretagogues: Growth Hormone Releasing Peptides" in Bercu BB, Walker RF editors, Growth Hormone Secretagogues, New York: Springer–Verlag, pp. 9–28 (1996).

V. De Gennaro Colonna, "Cardiac ischemia and impairment of vascular endothelium function in hearts from growth hormone–deficient rats: Protection by hexarelin", *European Journal of Pharmacology*, 334:201–207 (1997).

R. Deghenghi, "Small Peptides as Potent Releasers of Growth Hormone", *Journal of Pediatric Endocrinology & Metabolism*, 8:311–313 (1995).

R. Deghenghi, "The development of 'impervious peptides' as growth hormone secretagogues", *Acta Paediatr. Suppl.*, 423:85–7 (1997).

*Primary Examiner*—Michael P. Woodward
*Assistant Examiner*—David Lukton
*Attorney, Agent, or Firm*—Pennie & Edmonds LLP

[57] ABSTRACT

The present invention relates a number of novel peptide sequences which include a spirolactam, bicyclic or tricyclic peptidomimetic unit. The peptides disclosed herein exhibit binding to cardiac tissue and normalize cardiac pressure after administration, as well as diagnostic and therapeutic properties for certain neoplastic tissues. Importantly, these peptides do not release pituitary hormones such as corticotropin (ACTH) and growth hormone (GH), and are therefore devoid of certain unwanted side-effects. These peptides preferably have at least one lysine unit and at least one D-2-alkyl-trptophan unit.

10 Claims, 1 Drawing Sheet

FIG. 1

[125I]-Tyr-Ala-His-D-Mrp-Ala-Trp-D-Phe-Lys-NH2
(% of displacement)

DIAZASPIRO, AZEPINO AND AZABICYCLO THERAPEUTIC PEPTIDES

BACKGROUND OF THE INVENTION

The present invention relates to new peptides which include peptidomimetic units therein to stabilize and enhance their performance and bioavailbility.

Under the general term heart disease, a variety of cardiac ailments, including myocardial ischemia, heart failure and related vascular dysfunction, are treated with drugs such as organic nitrates, calcium channel blockers, β-adrenergic receptor antagonists, antiplatelet and antithrombotic agents, cardiac glycosides, angiotensin converting enzyme inhibitors and angiotensin receptor antagonists. A general review of the field is found, for example, in Goodman & Gilman's "The Pharmacologic Basis of Therapeutics", IX edition, McGraw-Hill, New York, (1996), chapters 32 and 34.

Recently, the protective effect of a peptide known as Hexarelin (also called examorelin) having the structure His-D-2-methyl-Trp-Ala-Trp-D-Phe-Lys-$NH_2$ was described in an article by V. De Gennaro Colonna et al., European J. Pharmacology, 334, (1997), 201–207. Hexarelin was found to reverse the worsening of cardiac dysfunction in growth hormone deficient rats. At least part of its beneficial effect on myocardial ischemia was attributed to the growth hormone liberating properties of the peptide.

Heart disease is an increasing health problem as the population at large ages, such that there is a need for additional drugs or agents for treatment of these conditions. A number of the peptides of the present invention are useful for this purpose.

SUMMARY OF THE INVENTION

The present invention relates new peptides which include a spirolactam, bicyclic or tricyclic peptidomimetic unit.

Many of the peptides disclosed herein also exhibit binding to cardiac tissue and have been found to normalize cardiac pressure after administration, thus imparting cardiac protecting activity by a mechanism which at the present is unknown. One common feature for these peptides is that at least one lysine unit is present. Also, those having at least one Mrp unit are preferred for this use.

BRIEF DESCRIPTION OF THE DRAWINGS

FIG. 1 is a graphical illustration of the ability of certain peptides to bind to heart tissue.

DETAILED DESCRIPTION OF THE PREFERRED EMBODIMENTS

In this description, the following abbreviations are used: D is the Dextro enantiomer, GH is growth hormone, Mrp is 2-Alkyl-Trp, where the Alkyl group has one to three carbon atoms, {IMA is imidazolylacetyl, GAB is γ-amino butyryl, INIP is isonipecotinyl, AIB is amino isobutyryl, Nal is β-naphthylalanine, TXM is tranexamyl (i.e., 4 (amino methyl)-cyclohexane carbonyl),} D-Hnh is D-1,2,3,4,5,6-hexahydronorharman-3-carboxylic acid, HAIC is (2S,5S)-5-amino-1,2,4,5,6,7-hexahydro-azepino[3,2,1-hi]indole-4-one-2-carboxylic acid, ATAB is 2-R(2β,5β,8β)-8-amino-7-oxo-4-thia-1-aza-bicyclo[3.4.0]nonan-2-carboxylic acid, and Ala, Lys, Phe, Trp, His, Thr, Cys, Tyr, Leu and Ile are the amino acids Alanine, Lysine, Phenylalanine, Tryptophan, Histidine, Threonine, Cysteine, Tyrosine, Leucine and Isoleucine, respectively.

These peptides are novel and have the formula:

A-B-D-Mrp-C-E in which:

A is H or Tyr;

B is a spirolactam substituent of the formula

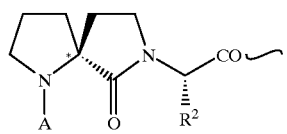

where, $R^2$ represents the side chain of any one naturally occurring amino acid, and the configuration at * is (R), (S) or a mixture thereof; a tricyclic substituent of the formula:

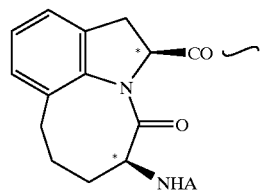

where the configuration at * is (S), (R) or a mixture thereof; a bicyclic substituent of the formula:

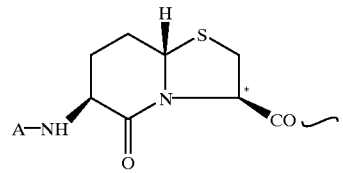

where the configuration at * is (R), (S) or a mixture thereof:

D-Mrp is Dextro-2-Alkyl-Trp, where the Alkyl group contains 1 to 3 carbon atoms and is preferably methyl;

C is Trp-Phe-Lys, D-Trp-Phe-Lys, Mrp-Phe-Lys, D-Mrp-Phe-Lys, Trp-Lys, D-Trp-Lys, Mrp-Lys, D-Mrp-Lys, Ala-Trp-D-Phe-Lys, Ala-Mrp-D-Phe-Lys, Ala-D-Mrp-D-Phe-Lys, D-Lys-Trp-D-Phe-Lys, D-Lys-Mrp-D-Phe-Lys, D-Lys-D-Mrp-D-Phe-Lys, or a tricyclic substituent of the formula:

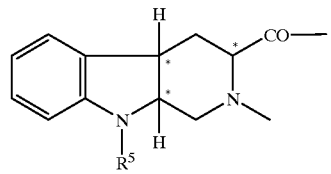

where $R^5$ is H or $SO_2Me$ and the configurations at * are either (R), (S), or a mixture thereof; and preferably E is Lys-$NH_2$ or —$NH_2$, provided that E is preferably Lys-$NH_2$ when C is the previously defined tricyclic substituent.

The preferred novel peptidomimetic containing peptides include the following:

[S,S-Spiro(Pro-Leu)]-D-Mrp-D-Trp-Phe-Lys-NH$_2$,
[S,S-Spiro(Pro-Leu)]-D-Mrp-Mrp-Lys-NH$_2$,
[S,S-Spiro(Pro-Leu)]-D-Mrp-Ala-Trp-D-Phe-Lys-NH$_2$,
[S,S-Spiro(Pro-Leu)]-D-Mrp-D-Lys-Trp-D-Phe-Lys-NH$_2$,
Tyr-[S,S-Spiro(Pro-Leu)]-D-Mrp-D-Lys-Trp-D-Phe-NH$_2$,
Tyr-[S,S-Spiro(Pro-Leu)]-D-Mrp-D-Lys-Trp-D-Phe-Lys-NH$_2$,
[S,S-Spiro(Pro-Ile)]-D-Mrp-D-Lys-Trp-D-Phe-Lys-NH$_2$,
[S,S-Spiro(Pro-Leu)]-D-Mrp-D-Hnh(SO$_2$CH$_3$)-Lys-NH$_2$,
HAIC-D-Mrp-D-Lys-Trp-D-Phe-Lys-NH$_2$, and
ATAB-D-Mrp-D-Lys-Trp-D-Phe-Lys-NH$_2$, where S,S-Spiro(Pro-Leu) and S,S-Spiro(Pro-Ile) is 4-Methyl-2S[6$^1$-oxo(5$^1$-S)1$^1$,7$^1$-diazaspiro[4,4]nonan-7$^1$-yl-]pentanoic acid. These substituents have the formula

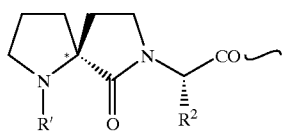

where R$^2$ is the side chain of Leu or Ile (see P. Ward et al., *J. Med Chem*. 33, 1848 (1990). Also, the tricyclic compound Hnh is obtained by conventional hydrogenation of the corresponding tetrahydronorharman-3-carboxylic acids of the formula:

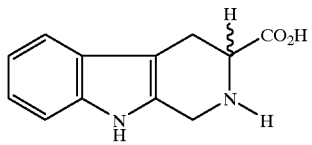

The peptidomimetic units which are advantageous for use in the peptides of the invention include those which are locking in a β-term configuration which mimic the natural amino acids. The spirolactam, bicyclic and tricyclic substituents defined above are preferred.

Pharmaceutically acceptable salts of the peptides of the present invention include can be used, if desired. Such salts would include organic or inorganic addition salts, including hydrochloride, hydrobromide, phosphate, sulfate, acetate, succinate, ascorbate, tartrate, gluconate, benzoate, malate, fumarate, stearate and pamoate salts. They can also be administered in controlled release formulations such as subcutaneous implants or intramuscular microcapsules and the like.

All these peptides can be conveniently synthesized according to the usual methods of peptide chemistry, such as by solid phase peptide synthesis, as described by E. Atherton and R. C. Sheppard in "Solid Phase Peptide Synthesis" IRL Press at Oxford University Press 1989, by solution phase synthesis as described by J. Jones in "The Chemical Synthesis of Peptides", Clarendon Press, Oxford 1994, or by both solid- and solution-phase methods, as known in the art.

The solid-phase synthesis starts from the C-terminal end of peptide. A suitable starting material can be prepared, for example, by attaching the required protected alpha-amino acid to a chloromethylated resin, a hydroxymethylated resin, a benzhydrylamine resin (BHA), or to a paramethylbenzhydrylamine resin (p-Me-BHA). As an example, an available chloromethylated resin is BIOBEADS® SX 1 by BioRad Laboratories, Richmond, Calif. The preparation of the hydroxymethyl resin is described by Bodansky et al., Chem. Ind. (London) 38, 15997 (1966). The BHA resin is described by Pietta and Marshall, Chem. Comm., 650 (1970) and is commercially available by Peninsula Laboratories Inc., Belmont, Calif.

After the starting attachment, the protecting group of the alpha-amino acid can be removed by means of different acid reagents, comprising trifluoroacetic acid (TFA) or hydrochloric acid (HCl) dissolved in organic solvents at room temperature. After the removal of the protecting group of the alpha-amino acid, the remaining protected amino acids can be coupled step by step in the desired order. Each protected amino acid can generally be reacted in excess of about three times using a suitable carboxyl activating group, such as dicyclohexylcarbodiimiide (DCC) or diisopropylcarbodiimide (DIC) dissolved, for example, in methylene chloride (CH$_2$Cl$_2$), dimethylformamide (DMF) or their mixtures. After the desired aminoacidic sequence has been completed, the desired peptide can be cleaved from the supporting resin by treatment with a reagent such as hydrogen fluoride (HF) which cleaves not only the peptide from the resin, but also the protecting groups of the lateral chains. When a chloromethylated resin or a hydroxymethylated resin is used, the treatment with HF leads to the formation of the terminal acid peptide in free form. When a BHA or p-Me-BHA resin is used, treatment with HF directly leads to the formation of the terminal amide peptide in free form.

Medicaments of these peptides can be administered to an animal, preferably a mammal and including a human. These medicaments can comprise a peptide of the present invention or a pharmaceutically acceptable salt thereof, or combinations of peptides of the present invention or pharmaceutically acceptable salts thereof, optionally, in admixture with a carrier, excipient, vehicle, diluent, matrix or delayed release coating. Examples of such carriers, excipients, vehicles and diluents, can be found in *Remington's Pharmaceutical Sciences*, 18th Edition, A. R. Gennaro, Ed., Mack Publishing Company, Easton, Pa., 1990.

These medicaments can be administered to animals, including humans, at a therapeutically effective dose which can be easily determined by one of skill in the art and which can vary according to the specie, age, sex and weight of the treated patient or subject. For example, in humans, when intravenously administered, the preferred dose falls in the range from about 1 μg to about 25 μg of total peptide per kg of body weight. When orally administered, typically higher amounts are necessary. For example, in humans for the oral administration, the dosage level is typically from about 30 μg to about 1000 μg of polypeptide per kg of body weight. The exact level can be easily determined empirically based on the above disclosure.

Any of the peptides of the present invention can be formulated by the skilled in the art to provide medicaments which are suitable for parenteral, buccal, rectal, vaginal, transdermal, pulmonary or oral routes by adjusting the dose as needed, such doses being in the range of from about 1 μg/kg to 1 mg/kg of body weight as noted above depending on the rate of absorption and the potency of the peptide.

These peptides possess useful therapeutic properties. In particular, many have cardioprotectant and in general beneficial cardiovascular properties. In addition, some have diagnostic and therapeutic properties for certain neoplastic tissues. Importantly, these peptides do not release pituitary hormones such as corticotropin (ACTH) and growth hormone (GH), and are therefore devoid of certain unwanted side-effects. For diagnostic purposes, the radioactive iodine derivatives on the initial tyrosine are particularly useful.

EXAMPLES

Example 1

Data is presented for the most preferred lysine containing peptides of the invention. The GH releasing effect was measured in rats according to the method described by R. Deghenghi et al., *Life Sci.* 54: 1321–1328 (1994). The cardiac protection of the instant peptides has been measured essentially as described in the publication by V. De Gennaro Colonna et al., *Europ. J. Pharmacol.* 334:201–207 (1997).

The binding abilities of certain peptides according to the invention compared to conventional peptides on human heart membranes are shown in FIG. 1. These data have been obtained according to the method of G. Muccioli et. al., *J. Endocrinology*, 156, 90 (1998). Data for the peptides used are shown in the graph using the following identifications.

| no. | peptide |
|---|---|
| A | [Spiro (S,S)-(Pro—Leu)]-D-Mrp-D-Trp—Phe—Lys—$NH_2$ |
| B | D-Mrp-D-Mrp—Phe—$NH_2$ |
| C | GAB-D-Mrp-D-Mrp—$NH_2$ |
| D | D-Mrp—Mrp—$NH_2$ |
| E | AIB-D-Mrp—Mrp—$NH_2$ |
| F | AIB-D-Mrp-D-Mrp—$NH_2$ |

Peptide A is in accordance with the invention, while peptides B-F are comparative. As shown in the figure, peptide A provided inhibition (i.e., displacement) of $^{125}$I-Tyr-Ala-His-D-Mrp-Ala-Trp-D-Phe-Lys-$NH_2$ in a proportion of about 75%, whereas peptides B-F only provided about 5 to less than 35%. The greater binding affinities for the peptides of the invention illustrate that these peptides directly operate on specific receptors of heart tissue to achieve normalization of cardiac pressure.

Example 2

[S,S-Spiro(Pro-Leu )]-D-Mrp-D-Trp-Phe-Lys-$NH_2$ By conventional solid phase synthesis, the title peptide was obtained and purified as the acetate salt. Theoretical molecular weight 915.2 +1; Found 915.5

Example 3

[S,S-Spiro(Pro-Leu )]-D-Mrp-Mrp-Lys-$NH_2$ Following the procedure of Example 2, the title peptide was similarly obtained as the acetate salt. Theoretical M.W. 782; Found 781.7

Example 4

[S,S-Spiro(Pro-Leu )]-D-Mrp-Ala-Trp-D-Phe-Lys-$NH_2$ The title compound was prepared in a similar procedure as in Example 2 and purified as the acetate salt. Theoretical M.W. 986.2 ; Found 986.2

Example 5

[S,S-Spiro(Pro-Leu)]-D-Mrp-D-Lys-Trp-D-Phe-Lys-$NH_2$ Similarly to Example 2, the title peptide was obtained as the acetate salt. Theoretical M.W. 1043.3; Found 1042.9

Example 6

Tyr-[S,S-Spiro(Pro-Leu)]-D-Mrp-D-Lys-Trp-D-Phe-Lys-$NH_2$ Similarly to Example 5, the title peptide was obtained as the acetate salt. Theoretical M.W. 1206.5; Found 1206.3

Example 7

As in Example 4, by a similar procedure, the title compound was obtain ed as the acetate salt. Theoretical M. W. 1043.3; Found 1043.0

Example 8

[S,S-Spiro(Pro-Leu)]-D-Mrp-D-Hnh($SO_2CH_3$)-$NH_2$, By a solution phase method, the title compound was obtained as the acetate salt. Theoretical M.W. 731.9; Found 732.4

Example 9

Haic-D-Mrp-D-Lys-Trp-D-Phe-Lys-$NH_2$ Similarly to Example 7, the title peptide was obtained as the acetate salt. Theoretical M.W. 1027.3; Found 1027.0

Example 10

Atab-D-Mrp-D-Lys-Trp-D-Phe-Lys-$NH_2$ Following a procedure similar to Example 8, the title compound was obtained as the acetate salt. Theoretical M.W. 1005.3; Found 1005.0

Example 11

The conversion of water soluble salts of any peptide described in Examples 2 to 10 above into water insoluble salts (e.g. pamoates or stearates) is obtained by treating an aqueous solution of the water soluble salts with the equivalent amount of an aqueous solution of sodium pamoate, or sodium stearate, and filtering the insoluble peptide salt which precipitates out of the solution. The dried insoluble salt can be used without further purification.

Examples 12–14

These examples illustrate preferred formulations for administration of the peptides of the invention.

Example 12

The peptide of Example 2 is lyophilized in sterile vials containing 100 micrograms of the peptide and 10 mg of mannitol as excipient. Water for injection is then used to dissolve the peptide into a formulation which can be injected i.v. into mammals with impaired cardiac function at a dose of 1 µg/kg body weight.

Example 13

The peptide of Example 3 is compounded with mannitol in a dry state (1:10) and then filled into soft gelatin capsules at a dose of 20 mg peptide (200 mg mannitol). The resulting capsule can be administered orally to mammals experiencing cardiac failure.

Example 14

The peptides of Examples 4 and 5 are dissolved in sterile water containing 0.05% of chlorocresol as a preservative. This solution can be administered intranasally at doses of 20 to 60 µg/kg twice or three times daily to mammals with impaired heart function so that the peptides can be rapidly absorbed.

What is claimed is:
1. A peptide of the formula:

in which:
B is a spirolactam substituent of the formula

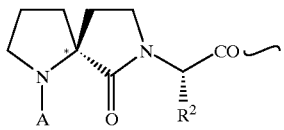

where A is H or Tyr, $R^2$ represents the side chain of any one naturally occurring amino acid, and the configuration at * is (R), (S) or a mixture thereof; a tricyclic substituent of the formula:

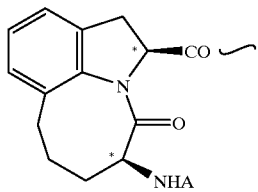

where A is H or Tyr and the configuration at * is (S), (R) or a mixture thereof; a bicyclic substituent of the formula:

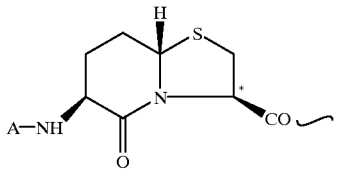

where A is H or Tyr and the configuration at * is (R), (S) or a mixture thereof; D-Mrp is Dextro-2-Alkyl-Trp, where the Alkyl group contains 1 to 3 carbon atoms;
C is Trp-Phe, D-Trp-Phe, Mrp-Phe, D-Mrp-Phe, Trp, D-Trp, Mrp, D-Mrp, Ala-Trp-D-Phe, Ala-Mrp-D-Phe, Ala-D-Mrp-D-Phe, D-Lys-Trp-D-Phe, D-Lys-Mrp-D-Phe, D-Lys-D-Mrp-D-Phe, or a tricyclic substituent of the formula:

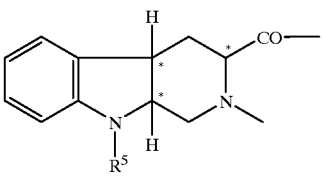

where $R^5$ is H or $SO_2Me$ and the configurations at * are either (R), (S), or a mixture thereof; and
E is Lys-$NH_2$ or -$NH_2$.

2. The peptide of claim 1 that contains a spirolactam substituent where $R^2$ is the side chain of Leu or Ile.
3. The peptide of claim 1 that contains a Lys unit.
4. The peptide of claim 1 that contains a D-Mrp unit.
5. The peptide of claim 1 specifically as

[S,S-Spiro(Pro-Leu)]-D-Mrp-D-Trp-Phe-Lys-$NH_2$,
[S,S-Spiro(Pro-Leu)]-D-Mrp-Mrp-Lys-$NH_2$,
[S,S-Spiro(Pro-Leu)]-D-Mrp-Ala-Trp-D-Phe-Lys-$NH_2$,
[S,S-Spiro(Pro-Leu)]-D-Mrp-D-Lys-Trp-D-Phe-Lys-$NH_2$,
Tyr-[S,S-Spiro(Pro-Leu)]-D-Mrp-D-Lys-Trp-D-Phe-$NH_2$,
Tyr-[S,S-Spiro(Pro-Leu)]-D-Mrp-D-Lys-Trp-D-Phe-Lys-$NH_2$,
[S,S-Spiro(Pro-Leu)]-D-Mrp-D-Hnh($SO_2CH_3$)-Lys-$NH_2$,
[S,S-Spiro (Pro-Ile)]-D-Mrp-D-Lys-Trp-D-Phe-Lys-$NH_2$,
HAIC-D-Mrp-D-Lys-Trp-D-Phe-Lys-$NH_2$, or
ATAB-D-Mrp-D-Lys-Trp-D-Phe-Lys-$NH_2$.

6. A pharmaceutical formulation suitable for parenteral use containing a peptide of claim 1 and a suitable carrier.
7. The pharmaceutical formulation of claim 6 wherein the peptide is present as a pharmaceutically acceptable water soluble salt.
8. The pharmaceutical formulation of claim 6 wherein the peptide is present as a pharmaceutically acceptable water insoluble salt.
9. The pharmaceutical formulation of claim 6 wherein the peptide is present in a matrix of a biodegradable material.
10. The pharmaceutical formulation of claim 6 wherein the peptide is present in an amount of 1 mg to 1 mg/kg per body weight of a mammal to which it is to be administered.

* * * * *

UNITED STATES PATENT AND TRADEMARK OFFICE
CERTIFICATE OF CORRECTION

PATENT NO. : 6,025,471

DATED : February 15, 2000

INVENTORS : Romano DEGHENGHI

It is certified that error appears in the above-identified patent and that said Letters Patent is hereby corrected as shown below:

In column 8, between lines 31 and 32 (claim 5, between lines 12 and 13), insert:
--[S,S-Spiro(Pro-Leu)]-D-Mrp-D-Hnh-($SO_2CH_3$)-$NH_2$,--.

Claim 5 should now read as follows:

5. The peptide of claim 1 specifically as
[S,S-Spiro(Pro-Leu)]-D-Mrp-D-Trp-Phe-Lys-$NH_2$,
[S,S-Spiro(Pro-Leu)]-D-Mrp-Mrp-Lys-$NH_2$,
[S,S-Spiro(Pro-Leu)]-D-Mrp-Ala-Trp-D-Phe-Lys-$NH_2$,
[S,S-Spiro(Pro-Leu)]-D-Mrp-D-Lys-Trp-D-Phe-Lys-$NH_2$,
Tyr-[S,S-Spiro(Pro-Leu)]-D-Mrp-D-Lys-Trp-D-Phe-$NH_2$,
Tyr-[S,S-Spiro(Pro-Leu)]-D-Mrp-D-Lys-Trp-D-Phe-Lys-$NH_2$,
[S,S-Spiro(Pro-Ile)]-D-Mrp-D-Lys-Trp-D-Phe-Lys-$NH_2$,
[S,S-Spiro(Pro-Leu)]-D-Mrp-D-Hnh($SO_2CH_3$)-Lys-$NH_2$,
[S,S-Spiro(Pro-Leu)]-D-Mrp-D-Hnh-($SO_2CH_3$)-$NH_2$,
HAIC-D-Mrp-D-Lys-Trp-D-Phe-Lys-$NH_2$, or
ATAB-D-Mrp-D-Lys-Trp-D-Phe-Lys-$NH_2$.

Signed and Sealed this

Twenty-sixth Day of December, 2000

*Attest:*

Q. TODD DICKINSON

*Attesting Officer*     *Director of Patents and Trademarks*